United States Patent [19]

Frischkorn et al.

[11] 4,375,556

[45] Mar. 1, 1983

[54] PROCESS FOR THE PREPARATION OF NAPHTHALENE-1,4-DICARBOXYLIC ACID

[75] Inventors: Hans Frischkorn; Erich Schinzel, both of Hofheim am Taunus, Fed. Rep. of Germany

[73] Assignee: Hoechst Aktiengesellschaft, Frankfurt, Fed. Rep. of Germany

[21] Appl. No.: 275,829

[22] Filed: Jun. 22, 1981

[30] Foreign Application Priority Data

Jun. 28, 1980 [DE] Fed. Rep. of Germany ....... 3024527

[51] Int. Cl.$^3$ ............................................. C07C 51/08
[52] U.S. Cl. ................................ 562/484; 260/438.1; 260/465 H; 562/485
[58] Field of Search ..................... 562/484; 260/438.1, 260/465 H

[56] References Cited

U.S. PATENT DOCUMENTS

| | | | |
|---|---|---|---|
| 2,716,646 | 8/1955 | Willett et al. | 260/465 H |
| 2,979,526 | 4/1961 | Gasson et al. | 562/484 |
| 3,113,964 | 12/1963 | Farkas et al. | 562/484 |
| 3,116,313 | 12/1963 | Fierce et al. | 260/465 H |
| 3,781,343 | 12/1973 | Norton | 562/484 |

*Primary Examiner*—Natalie Trousof
*Assistant Examiner*—Vera C. Clarke
*Attorney, Agent, or Firm*—Connolly and Hutz

[57] ABSTRACT

A process for the preparation of naphthalene-1,4-dicarboxylic acid, which comprises reacting 1,4-dihalogenonaphthalene with at least 2 moles of copper-I cyanide per mole of dihalogenonaphthalene in a polar, aprotic solvent and subjecting the copper salt complex of 1,4-dicyanonaphthalene thus obtained to alkaline hydrolysis.

3 Claims, No Drawings

PROCESS FOR THE PREPARATION OF NAPHTHALENE-1,4-DICARBOXYLIC ACID

It is already known that naphthalene-1,4-dicarboxylic acid can be prepared by hydrolysis of 1,4-dicyanonaphthalene [compare R. Scholl and H. Neumann, Ber. 55 (1922), 121 and E. F. Bradbrook and R. P. Linstead, J. Chem. Soc. (London) 1936, 1739-1744]. The processes described in these publications for the preparation of the dinitrile use suitable naphthalenesulfonic acids as starting materials, which are converted into 1,4-dicyanonaphthalene in a potassium cyanide melt. However, these processes require extreme conditions and lead to a relatively large amount of dark-colored by-products, and are therefore not particularly suitable for industrial production of naphthalene-1,4-dicarboxylic acid.

It has now been found that naphthalene-1,4-dicarboxylic acid can be prepared in a high purity and in a manner which can easily be carried out on an industrial scale by reacting 1,4-dihalogenonaphthalene with at least 2 moles of copper-I cyanide per mole of dihalogenonaphthalene in polar aprotic solvents, if appropriate in the presence of catalytic amounts of potassium iodide and copper sulfate, and subjecting the copper salt complex of 1,4-dicyanonaphthalene thus obtained to alkaline hydrolysis.

Suitable dihalogenonaphthalenes are 1,4-dichloronaphthalene, which has already been described in the literature a long time ago (compare German Reichspatent No. 286,489), and 1,4-dibromonaphthalene, which has also already been known for a long time (compare J. S. Salkind and S. B. Faerman, Journal of the Russian Physical Society, Chemical Section 62 (1930), 1021-1032). Both the dihalogenonaphthalenes can be prepared in a simple manner from the parent substance naphthalene, which is readily accessible on an industrial scale. The amount of copper-I cyanide used varies between 2 and 2.5 moles per mole of the dihalogeno compound. The polar aprotic solvent used is N-methylacetamide, dimethylacetamide, dimethylsulfoxide, N-methylpyrrolidone, hexamethylphosphoric acid triamide, quinaldine or, preferably, dimethylformamide or quinoline. In the case of the dibromo compound, dimethylformamide can advantageously be used. The dichloro compound, which reacts more slowly, is preferably reacted in the higher-boiling solvent quinoline. The reaction is carried out at temperatures from 150° to 250° C., advantageously at the boiling point of the solvent employed. It is also advantageous to accelerate the reaction by adding a catalyst. A mixture of potassium iodide and copper sulfate can be used for this purpose.

In this reaction, 1,4-dicyanonaphthalene is obtained as a copper-I salt complex having the following composition:

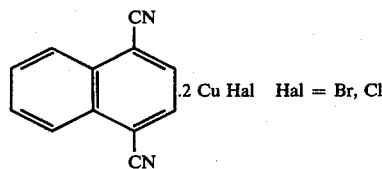

and can be isolated after the reaction mixture has been cooled and after water or a low-boiling solvent has been added. Lower alcohols, preferably methanol or ethanol, are used as the low-boiling polar solvent.

The still moist copper-salt complex is then directly subjected to alkaline hydrolysis with a strong alkali, for example with excess 10-35% strength sodium hydroxide solution, at the boiling point by known methods, without the 1,4-dicyano-naphthalene being liberated. The pH value of the solution is then adjusted to 7 to 8 and the copper oxide which thereby precipitates quantitatively is separated off. The naphthalenedicarboxylic acid is separated out of the filtrate by further addition of mineral acid up to a pH value of 2, and is separated off.

Working up can also be carried by a procedure in which isolation of the copper salt complex of 1,4-dicyanonaphthalene is dispensed with and, when the replacement of cyanide by halogen has ended, the reaction mixture is hydrolyzed directly with a strong alkali, such as, for example, 10-35% strength sodium hydroxide solution.

If quinoline or quinaldine is used as the solvent, this can be distilled off with steam during the hydrolysis.

The process according to the invention can also be carried out by using, as the starting substances, 1,4-dihalogenonaphthalenes which are still contaminated with other dihalogenonaphthalenes which are position isomers, and subjecting the resulting crude naphthalene-1,4-dicarboxylic acid to purification. Possible dihalogenonaphthalenes which are position isomers and which can be contained in the 1,4-dihalogenonaphthalene are, above all, the 1,5- and 2,6- as well as the 2,7-isomers. For purification, the crude naphthalene-1,4-dicarboxylic acid is dissolved in a suitable solvent, after being dried, and the sparingly soluble isomers, that is to say naphthalene-1,5- and/or -2,6- and/or -2,7-dicarboxylic acid are separated off by filtration. Low-boiling glycol monoethers, such as ethylene glycol monomethyl ether and ethylene glycol monoethyl ether, are chiefly suitable for the purification operation.

The naphthalene-1,4-dicarboxylic acid obtained by the process according to the invention is used as a precursor for dyestuffs, UV absorbers, scintillators and optical brighteners. It is free from colored impurities and can be employed directly for further synthesis.

The following examples illustrate the invention in more detail. The temperatures are given in °C.

EXAMPLE 1

98.6 parts by weight of 1,4-dichloronaphthalene with a solidification point of 60°, 100 parts by weight of copper-I cyanide (67-71% of copper), 2 parts by weight of anhydrous copper sulfate and 2 parts by weight of potassium iodide are introduced into 330 parts by weight of anhydrous quinoline. The mixture is then heated under reflux to 235°-240°, with stirring, for 20 hours, a homogeneous dark solution being formed. After the reaction mixture has been cooled to 120°-130°, 1,125 parts by weight of 20% strength sodium hydroxide solution are added and the yellowish-brown suspension formed is heated under reflux, the refluxing liquid being passed over a suitable phase separator and the phase with the higher specific gravity, that is to say water-containing quinoline, is stripped off. After the 1,4-dicyanonaphthalene-copper salt complex has been completely hydrolyzed or all of the quinoline has been driven off (after about 6 hours), the mixture is allowed to cool to 80° and is neutralized to pH 7-8 with about 465 parts by weight of concentrated hydrochloric acid (about 31% strength), and the copper oxide sludge which has separated out is filtered off and rinsed with water. The reaction product, that is to say naphthalene-1,4-dicarboxylic acid, is precipitated in the filtrate by adding about 105 parts by weight of concentrated hydrochloric acid (31% strength), and is filtered off and washed with water until free from chlorine ions. After the product has been dried, 87 parts by weight of a virtually colorless dicarboxylic acid with a melting point of 315°–320° are obtained.

EXAMPLE 2

143 parts by weight of 1,4-dibromonaphthalene with a solidification point of 78° and 100 parts by weight of copper-I cyanide (67–71% of copper) are introduced into 305 parts by weight of dimethylformamide. The mixture is then heated to 150°–160° under reflux, with stirring, for 4 hours, a solution initially being obtained and the 1,4-dicyanonaphthalene-copper bromide complex then gradually precipitating. After the reaction mixture has been cooled to about 60° C., it is diluted with 635 parts by weight of methanol, subsequently stirred at room temperature for about one hour and filtered and the material on the filter is washed with about 160 parts by weight of methanol. The 1,4-dicyanonaphthalene-copper bromide complex thus isolated is introduced into 680 parts by weight of 33% strength sodium hydroxide solution and the mixture is heated to 100° to 105°, with stirring and whilst distilling off the methanol introduced. Hydrolysis is then carried out by heating the mixture under reflux for 6 hours and the reaction mixture is cooled to about 80° and, after being diluted with 335 parts by weight of water, is adjusted to pH 7.0–7.5 with about 460 parts by weight of concentrated hydrochloric acid. The copper oxide sludge which has separated out is filtered off and rinsed with about 500 parts by weight of water in portions. The naphthalene-1,4-dicarboxylic acid is precipitated at pH 2 in the filtrate by the addition of about 130 parts by weight of concentrated hydrochloric acid, and is then filtered off. The product is washed with water until free from chlorine ions to give, after drying, 90 parts by weight of a virtually colorless acid with a melting point of 315°–320°.

EXAMPLE 3

The procedure followed is as under Example 2, but 143 parts by weight of crude 1,4-dibromonaphthalene, such as can be obtained by reacting bromine with naphthalene in glacial acetic acid, are employed. This crude material has a solidification point of 62°–64° and contains up to 25% of the 1,5-isomer. After the product has been dried, 86 parts by weight of crude naphthalene-1,4-dicarboxylic acid which can contain up to 20% of the isomeric 1,5-dicarboxylic acid are obtained. For purification, the crude acid is heated to the boiling point in 1,660 parts by weight of ethylene glycol monomethyl ether for about one hour, in order to obtain a complete solution of the 1,4-dicarboxylic acid, and the mixture is cooled to room temperature and, after being subsequently stirred for one hour, is filtered. A contaminated naphthalene-1,5-dicarboxylic acid remains as the residue. About 1,400 parts by weight of ethylene glycol monomethyl ether are distilled off from the filtrate, and 1,400 parts by weight of water are added to the bottom product, whereupon the naphthalene-1,4-dicarboxylic acid precipitates completely. The product is filtered off and rinsed with about 100 parts by weight of water. After the product has been dried, 67 parts by weight of a colorless naphthalene-1,4-dicarboxylic acid with a melting point of 315°–320° are obtained.

We claim:

1. A process for the preparation of naphthalene-1,4-dicarboxylic acid, which comprises reacting a 1,4-dihalogenonaphthalene with at least 2 moles of copper-I cyanide per mole of dihalogenonaphthalene in a polar, aprotic solvent at a temperature of from 150° to 250° C. and subjecting the copper salt complex of 1,4-dicyanonaphthalene thus obtained to alkaline hydrolysis.

2. A process as claimed in claim 1, wherein the copper salt complex of 1,4-dicyanonaphthalene is precipitated by the addition of water or a low-boiling polar solvent and is separated off and hydrolyzed.

3. A process as claimed in claim 1, wherein the copper salt complex of 1,4-dicyanonaphthalene is hydrolyzed directly in the reaction mixture, after replacement of the cyanide, without prior isolation.

* * * * *